(12) United States Patent
Godlewski

(10) Patent No.: US 8,175,746 B2
(45) Date of Patent: May 8, 2012

(54) WEIGHT-BASED DISPENSING SYSTEM

(75) Inventor: Peter Godlewski, San Clemente, CA (US)

(73) Assignee: Carefusion 303, Inc., San Diego, CA (US)

( * ) Notice: Subject to any disclaimer, the term of this patent is extended or adjusted under 35 U.S.C. 154(b) by 360 days.

(21) Appl. No.: 12/494,202

(22) Filed: Jun. 29, 2009

(65) Prior Publication Data
US 2010/0327001 A1    Dec. 30, 2010

(51) Int. Cl.
*G06F 17/00* (2006.01)
(52) U.S. Cl. .......... 700/236; 700/242; 700/244
(58) Field of Classification Search .......... None
See application file for complete search history.

(56) References Cited

U.S. PATENT DOCUMENTS

| | | | |
|---|---|---|---|
| 4,108,363 A * | 8/1978 | Susumu | 221/150 HC |
| 5,774,865 A | 6/1998 | Glynn | |
| 5,853,244 A * | 12/1998 | Hoff et al. | 700/265 |
| 6,539,281 B2 * | 3/2003 | Wan et al. | 700/236 |
| 6,694,221 B2 * | 2/2004 | Chavez et al. | 700/236 |
| 7,428,447 B2 * | 9/2008 | Stonikas et al. | 700/236 |
| 7,597,259 B2 * | 10/2009 | Nishikawa et al. | 235/441 |
| 2002/0097156 A1 | 7/2002 | Broas | |
| 2003/0019879 A1 | 1/2003 | Hubicki | |
| 2006/0058917 A1 | 3/2006 | Vonk et al. | |

FOREIGN PATENT DOCUMENTS

| | | |
|---|---|---|
| DE | 102005031269 | 12/2006 |
| WO | WO 01/47466 | 7/2001 |

* cited by examiner

*Primary Examiner* — Timothy Waggoner
(74) *Attorney, Agent, or Firm* — McDermott Will & Emery LLP

(57) ABSTRACT

A weight-based dispensing system is disclosed. The system includes a platform and a container, coupled to the platform, including a lid configured to move between a closed state restricting access to items in the container and an open state allowing access to the items in the container. The system also includes at least two weight sensors, wherein each of the weight sensors is coupled to the platform and is configured to determine a change in weight on the platform, and a controller configured to determine a change in the number of items in the container based on the state of the lid and the change in weight on the platform. A method for dispensing items is also disclosed.

22 Claims, 6 Drawing Sheets

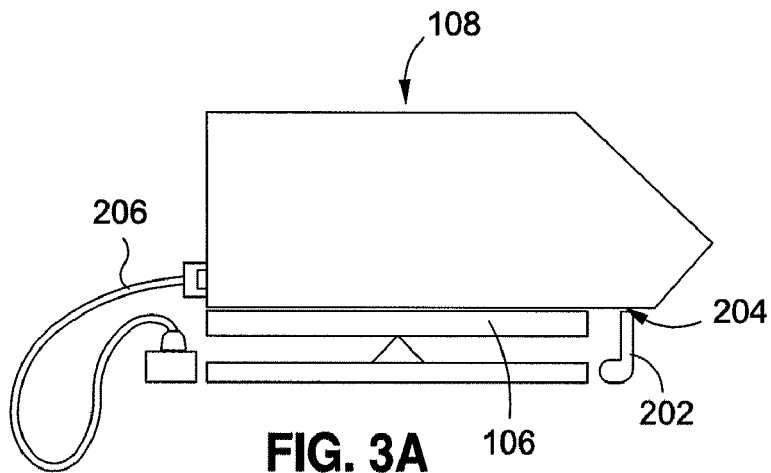
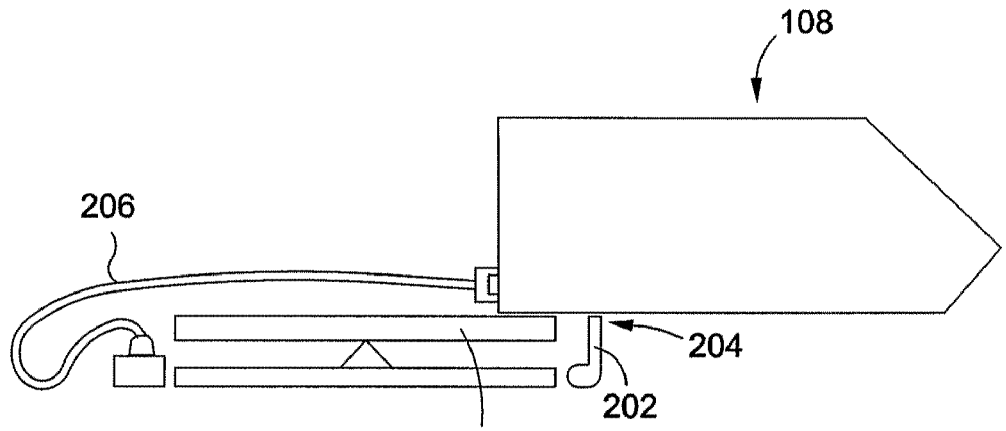
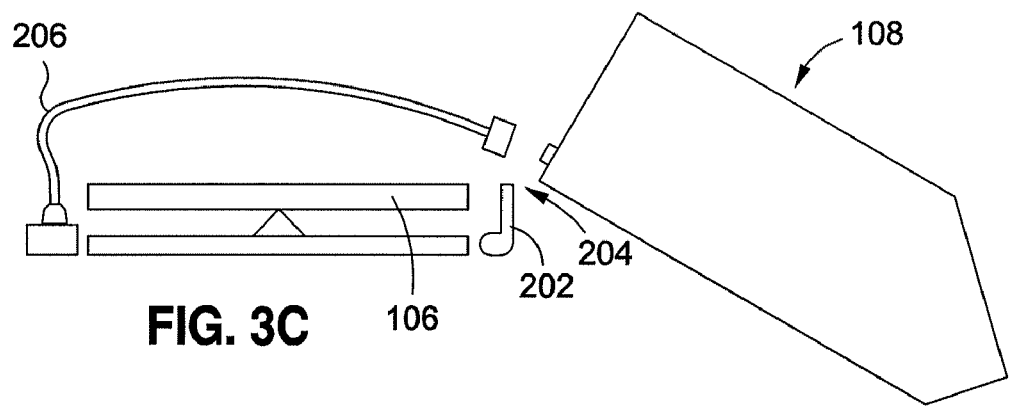

WEIGHT-BASED DISPENSING SYSTEM

BACKGROUND

1. Field

The present disclosure generally relates to systems and methods for inventory management, and, in particular, relates to tracking the inventory of items in containers.

2. Description of the Related Art

It is well known in the medical community, and in particular, in hospitals, to store medications and other medical supplies in a centralized area or station for dispensing and administering the medications or supplies to patients. These stations often require user interaction to track quantity of each medication that is stored in, added to, or removed from the station.

For example, many stations require a user to gain access to the medications in the station and manually press a button for each and every medication taken from the station, even though the user has access to and may remove many medications from the station at once. In practice, users are not always compliant in pressing the button for each removal of medication, often due to forgetfulness. Such manual button pressing requires continuous monitoring and messaging to enforce and maintain a high level of compliance by users.

As another example, other types of stations rely on radio-frequency identification (RFID) tags on medications and an RFID tracking device in the station to track the quantity of the medications in the station. In such stations, the RFID tracking device is able to track the movement (e.g., removal or addition) of medications based on their individual RFID tags. The management of such stations is complex. Each medication must be tagged with an RFID tag, and each RFID tag must be programmed correctly and validated. This process, including the cost of RFID tags, is relatively expensive, and as such RFID tracking technology is often only used on high cost medications. Consequently, low cost medications, which often are a majority of the items stored in stations, remain untracked.

SUMMARY

A low-cost solution that does not require interaction by users is needed to track medications or other supplies in medication and supply stations. The weight-based dispensing system disclosed herein provides a low-cost solution for tracking all of the medications in a medication station based on the change in weight of the medications and the container in the medication station that is being accessed.

According to certain embodiments of the present disclosure, a weight-based dispensing system is provided. The system includes a platform and a container, coupled to the platform, including a lid configured to move between a closed state restricting access to items in the container and an open state allowing access to the items in the container. The system also includes at least two weight sensors, wherein each of the weight sensors is coupled to the platform and is configured to determine a change in weight on the platform, and a controller configured to determine a change in the number of items in the container based on the state of the lid and the change in weight on the platform.

According to certain embodiments of the present disclosure, a weight-based dispensing system is provided. The system includes a cabinet. The cabinet includes a plurality of shelves. Each shelf includes a common platform, and at least one container, coupled to the common platform, including a lid configured to move between a closed state restricting access to items in the at least one container and an open state allowing access to the items in the at least one container. Each shelf also includes at least two weight sensors, wherein each of the weight sensors is coupled to the common platform and is configured to determine a change in weight on the common platform. The cabinet also includes a controller configured to determine a change in the number of items in the at least one container based on the state of the lid and the change in weight on the platform.

According to certain embodiments of the present disclosure, a method for dispensing items is provided. The method includes providing access to a plurality of items in a container coupled to a platform, and determining whether the weight of the container has changed using at least two weight sensors coupled to the platform. The method also includes determining, based on the weight of the container, whether there is a change in the number of items in the container.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 3A-3C illustrate a side view in the direction of arrows III-III of FIG. 2 of the container of the weight-based dispensing system of FIG. 2 in the process of being removed from the platform and decoupled from the communications connector.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

Figure 1A:
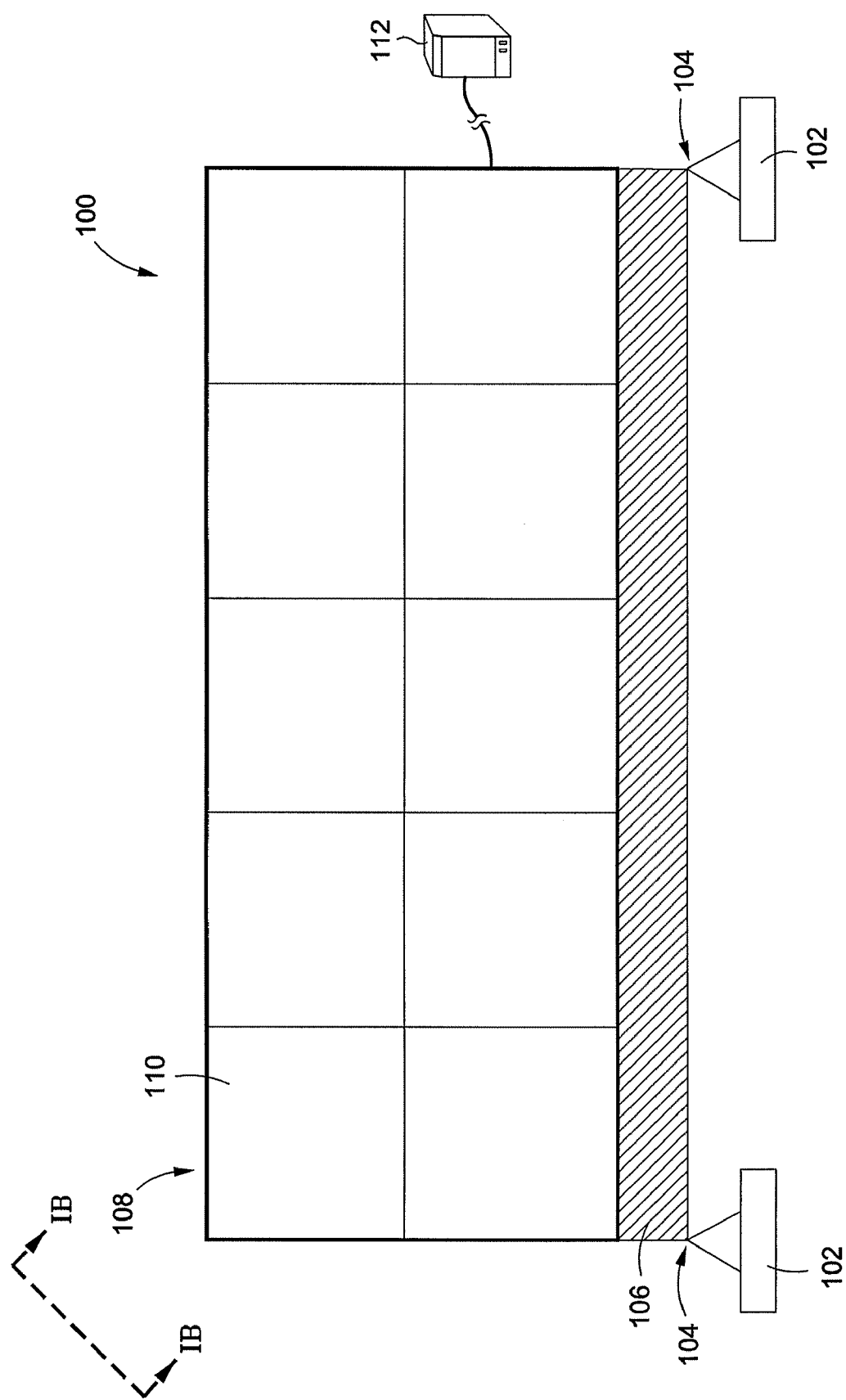
FIG. 1A illustrates a front view of a weight-based dispensing system according to certain embodiments.

FIG. 1A illustrates a front view of a weight-based dispensing system 100 according to certain embodiments. The weight-based dispensing system 100 includes a platform 106, a plurality of containers 108 on the platform 106, two weight sensors 102, and a controller 112.

Each container 108 is configured to store a plurality of items, such as medications. Each container 108 includes a lid 110 that is configured to move between a closed state restricting access to the medications in the container 108 and an open state allowing access to the medications in the container 108. For example, in certain embodiments, each container 108 includes a self-contained latching system well known to those of skill in the art that is controlled by the controller 112 (e.g., by a motorized cam) and configured to move by electronic activation between a closed state restricting access to the medications in the container 108 and an open state allowing access to the medications in the container 108. In certain embodiments, the latching system can be wirelessly activated. A self-contained access system such as a wireless latching system advantageously incorporates most moving pieces within each container 108, thereby facilitating more accurate measurement by the weight sensors 102. In certain embodiments, other systems can be used to control access to each container 108.

Each of the two weight sensors 102 is configured, either jointly or individually, to determine the weight of the platform 106 and the containers 108 (including any medications in the containers 108) on the platform 106. Each of the two weight sensors 102 is placed below the platform 106 on which the containers 108 reside. In certain embodiments, each of the two weight sensors 102 is placed substantially near an end of the platform 106 such that the contact point 104 of each weight sensor 102 is in contact with the platform 106 at the end of the platform 106. This placement of the weight sensors 102 facilitates the accuracy of weight measurement by the weight sensors 102 by reducing the effect of pivot and torque on the weight measurement. In certain embodiments, in order to further facilitate the accuracy of weight measurement, the contact point 104 of each weight sensor 102 is the tip of a pyramid shaped portion of the weight sensor 102. In certain embodiments (not illustrated), more than two weight sensors 102 may be used. The weight sensors 102 are coupled to the platform 106 in certain embodiments.

The controller 112 is configured to provide access to the containers 108 by electronically moving the lid 110 of each container 108 from the closed state to the open state. The controller 112 can be, for example, a computer system that includes an input/output device (e.g., a communications bus), a processor, and memory. In certain embodiments, the controller 112 uses a latching system to unlatch the lid 110 of each container 108, thereby allowing each container 108 to be accessed by a user, and after the controller 112 detects the lid 110 of one container has been moved by the user, the controller 112 may then latch the lids 110 of all remaining containers 108 closed. By allowing the user to remove medications from only one container 108 at a time, the controller 112 can accurately determine the amount of medication removed from a specific container 108. Hence, the controller 112 is configured to determine a change in the number of items in the accessible container 108 based on the state of the lid 110 and the change in weight on the platform 106.

Figure 1B:
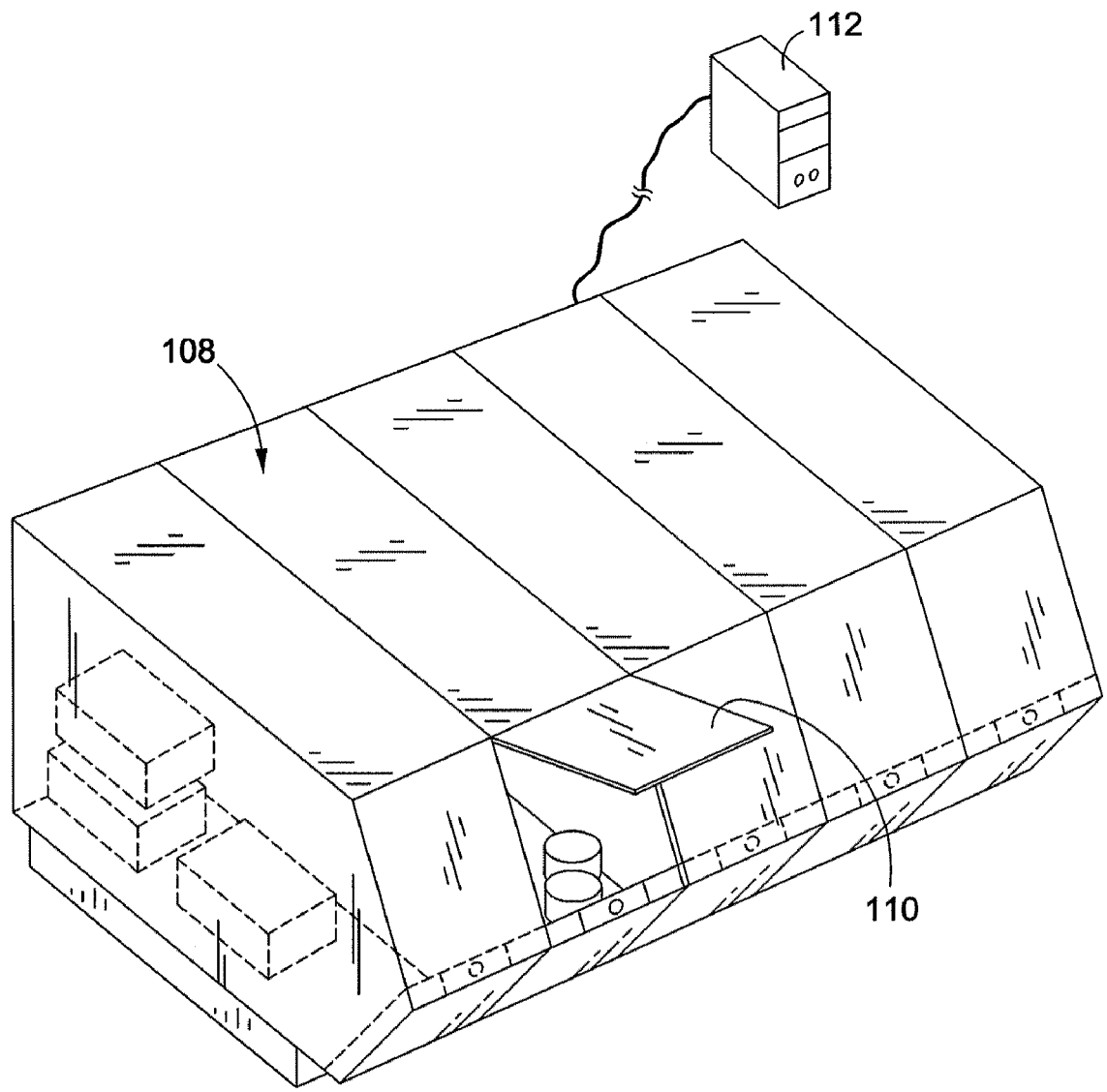
FIG. 1B illustrates a top perspective view of the weight-based dispensing system of FIG. 1A in the direction of arrows IB-IB of FIG. 1A.

For example, a user seeks to access a container 108 to remove a medication. The weight reading of the weight sensors 102 before access by the user is 104 grams (e.g., because the weight reading includes the weight of a plurality of containers 108, the medications the containers 108 contain, and the platform 106). The controller 112 then provides the user with access to only one container 108 on the platform 106, such as after the user has provided appropriate authentication information (e.g., user identification, patient identification, and/or identification of additional codes for a transaction), by moving the lid 110 of the container 108 from a closed state to an open state, as illustrated in FIG. 1B. The accessible container 108 contains only four identical tablets of aspirin, each weighing one gram, for a total weight of four grams. After the user opens the lid 110 of the container 108, the controller 112 restricts access to all remaining containers 108. The user, after having accessed the container 108, moves the lid 110 from the open state back to the closed state, and the controller 112 detects that the lid 110 of the only open container 108 has been closed. The weight reading of the weight sensors 102 after access by the user is 103 grams, which is a reduction in weight of one gram from the previous reading (e.g., change in weight=prior weight reading minus current weight reading). In certain embodiments, the controller 112 can account for margins of error in the weight measurement. Because the only accessible container contained aspirin tablets weighing one gram each, and because the total change in weight by the weight sensors 102 after access by the user is a reduction of one gram, the controller 112 determines that one aspirin tablet was removed from the container 108 of aspirin. The process may then be repeated by the user.

As another example, the user seeks to access another container 108 for a medication. The weight reading of the weight sensors 102 before access by the user is 126 grams. The controller 112 provides the user with access to only one container 108 on the platform 106 by moving the lid 110 of the container 108 from a closed state to an open state. The opened container 108 contains only 8 identical tablets of ibuprofen, each weighing two grams, for a total weight of 16 grams. After the user opens the lid 110 of the container 108, the controller 112 restricts access to all remaining containers 108. The user, after having accessed the container 108, moves the lid 110 from the open state back to the closed state, and the controller 112 detects that the lid 110 of the only open container 108 has been closed. The weight reading of the weight sensors 102 after access by the user is 138 grams. Because the only accessible container contained ibuprofen tablets weighing two grams each, and because the total change in weight by the weight sensors 102 after access by the user is an increase of 12 grams, the controller 112 determines that six ibuprofen tablets were added to the container 108 of ibuprofen.

Figure 2A:
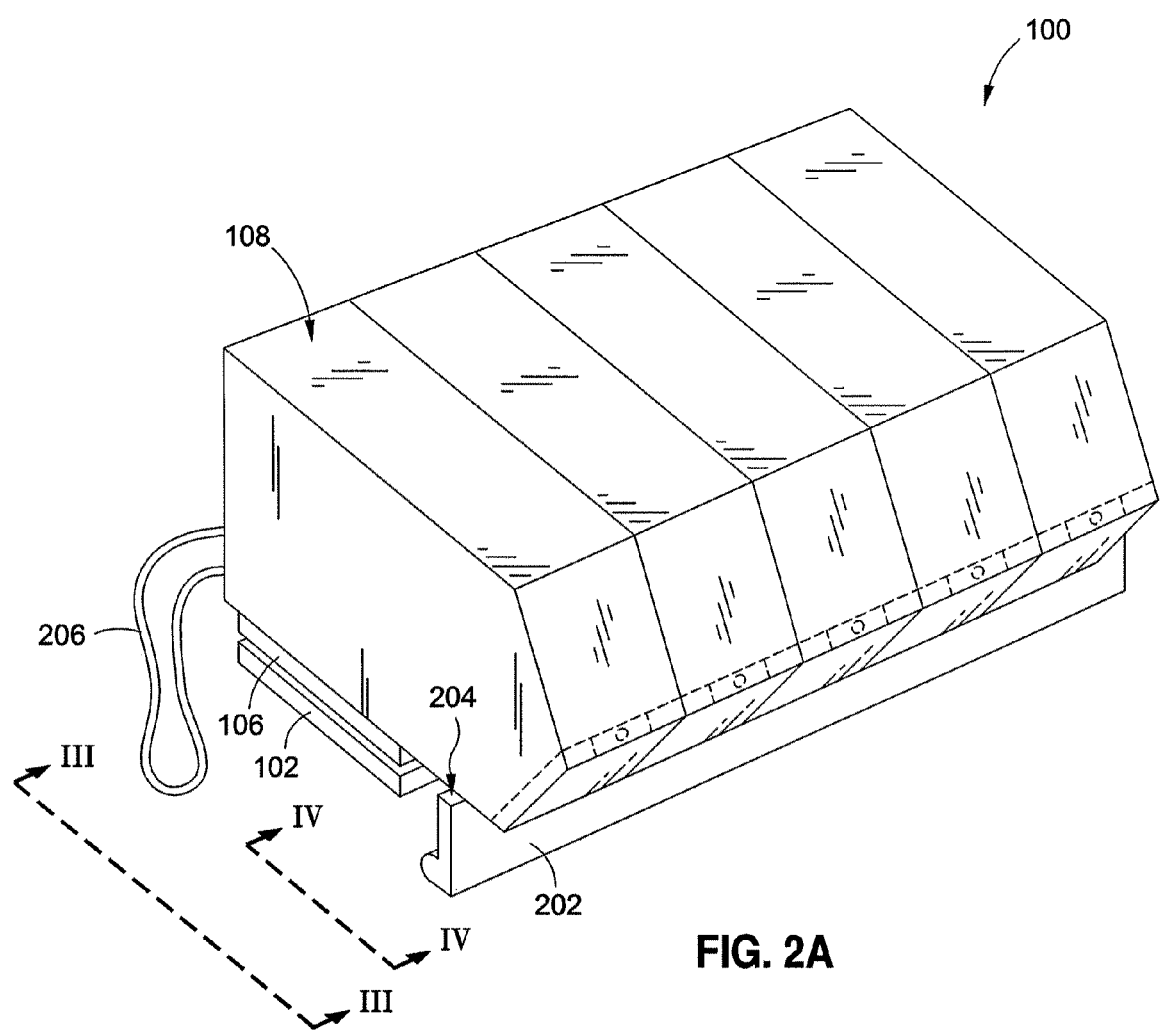
FIG. 2A illustrates a top perspective view of the weight-based dispensing system of FIG. 1A in the direction of arrows IB-IB of FIG. 1A, showing a communications connector and access panels.
Figure 2B:
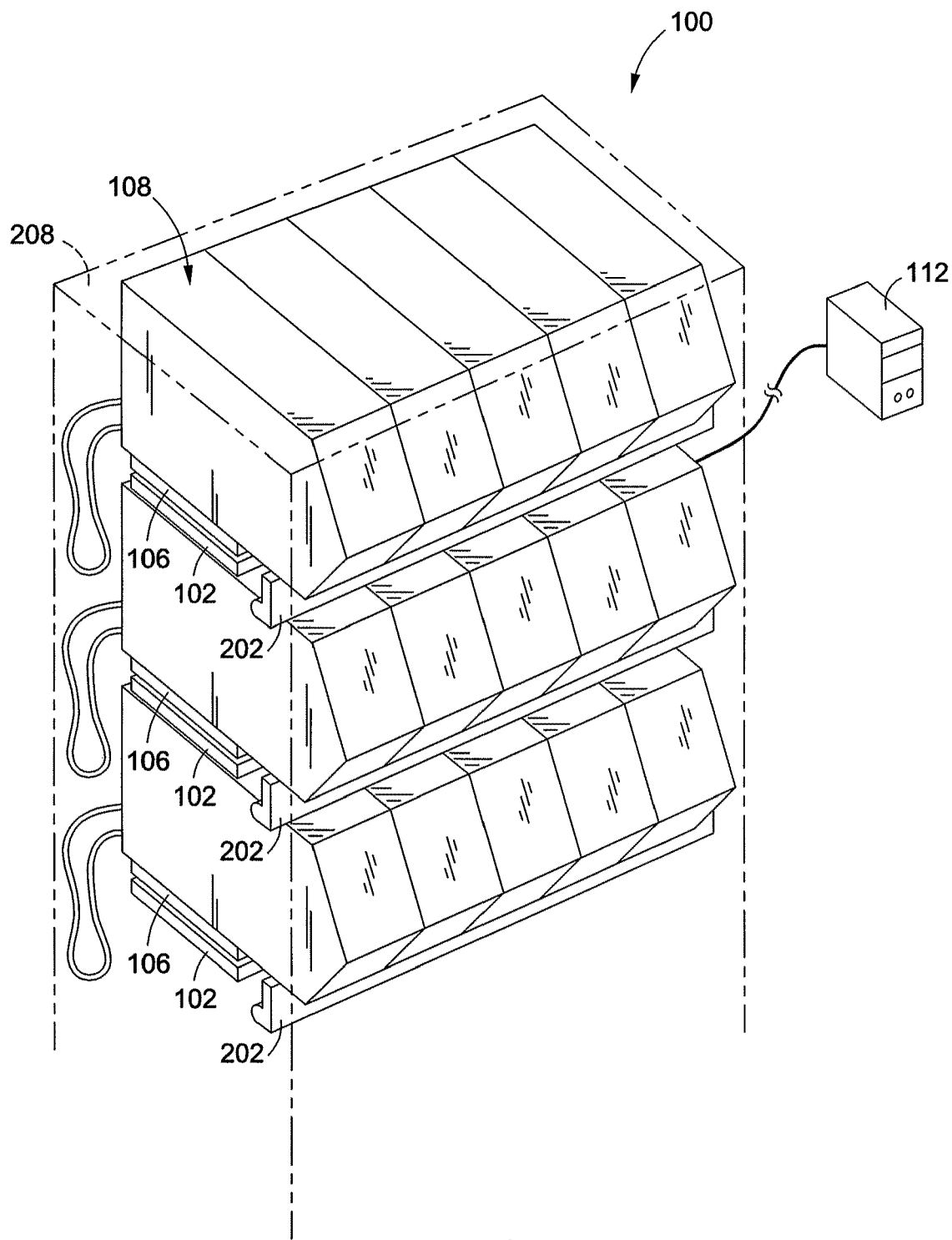
FIG. 2B illustrates a top perspective view of the weight-based dispensing system of FIG. 1A in the direction of arrows IB-IB of FIG. 1A, showing a cabinet including a plurality of platforms, weight sensors, access panels, and containers.

FIG. 2A illustrates a top perspective view of the weight-based dispensing system 100 of FIG. 1A in the direction of arrows IB-IB of FIG. 1A, further including a communications connector 206 and access panel 202. In certain embodiments, the weight-based dispensing system 100 can be included in a cabinet 208 (illustrated in phantom) having a plurality of platforms 106, wherein each platform 106 includes a plurality of containers 108 with corresponding weight sensors 102 and access panels 202, and at least one controller 112, as illustrated in FIG. 2B.

Returning to FIG. 2A, the communications connector 206 is configured to couple each of the containers 108 to the controller 112, such as to allow the controller 112 to, for example, control access to the containers 108. The illustrated communications connector 206 is a wired connection between the containers 108 and the controller 112. In such embodiments, the impact of the weight and placement of the communications connector 206 is considered as a factor in the measurement taken by the weight sensors 102. As illustrated herein, the communications connector 206 is a cable connecting the containers 108 and the controller. In certain embodiments, the communications connector 206 can include a pin connector. In certain embodiments, the communications connector 206 can include a wireless connection. In such embodiments, the latching system controls can be powered by an on-board battery.

Access panel 202 restricts access to the weight sensors 102. When the access panel 202 is a closed state, as illustrated, access to the weight sensors 102 is restricted. When the access panel is in an opened state, access to the weight sensors 102 is allowed, so as to allow for configuring or replacement of the weight sensors 102. In certain embodiments, the access panel 202 is controlled by the controller 112, e.g., by using a motorized cam. In certain embodiments, the access panel 202 is also used to control access to the containers 108, as discussed below.

A container clearance space 204 is present between a surface of the containers 108 and each access panel 202 so as to allow for movement of the containers 108. Specifically, FIGS. 3A-3C illustrate a side view in the direction of arrows III-III of FIG. 2 of the container 108 of the weight-based dispensing system 100 of FIG. 2 being removed from the platform 106 and decoupled from the communications connector 206. As illustrated in FIG. 3B, a user may begin to remove the container 108 from its original position on the platform 106 illustrated in FIG. 3A. A user may obtain access to move the container 108 by, for example, using a key, or by obtaining access from the access panel 202. Movement of the container 108 is facilitated by the container clearance space 204 between the access panel 202 and the container 108. Once the container 108 is substantially removed from the platform 106, the communications connector 206 can be decoupled from the container 108 (illustrated in FIG. 3C).

In certain embodiments, in order to facilitate decoupling of the communications connector 206 from the container 108, the communications connector 206 can be located in front (not illustrated) of the container 108 instead of behind the container 108, as illustrated in FIGS. 3A-3C. Placing communications connector 206 in front of the weight sensors 102 may increase the ease with which the weight-based dispensing station 100 is serviced and/or configured, the simplicity of access to the communications connector 206, and reduce the length (and therefore cost) of any cabling used for the communications connector 206. In certain embodiments, the communications connector 206 may be integrated into the platform 106, such as in a docking configuration well known to those of skill in the art, to reduce and/or eliminate the use of cables and to create a more secure coupling between the communications connector 206 and the container 108.

Figure 4:
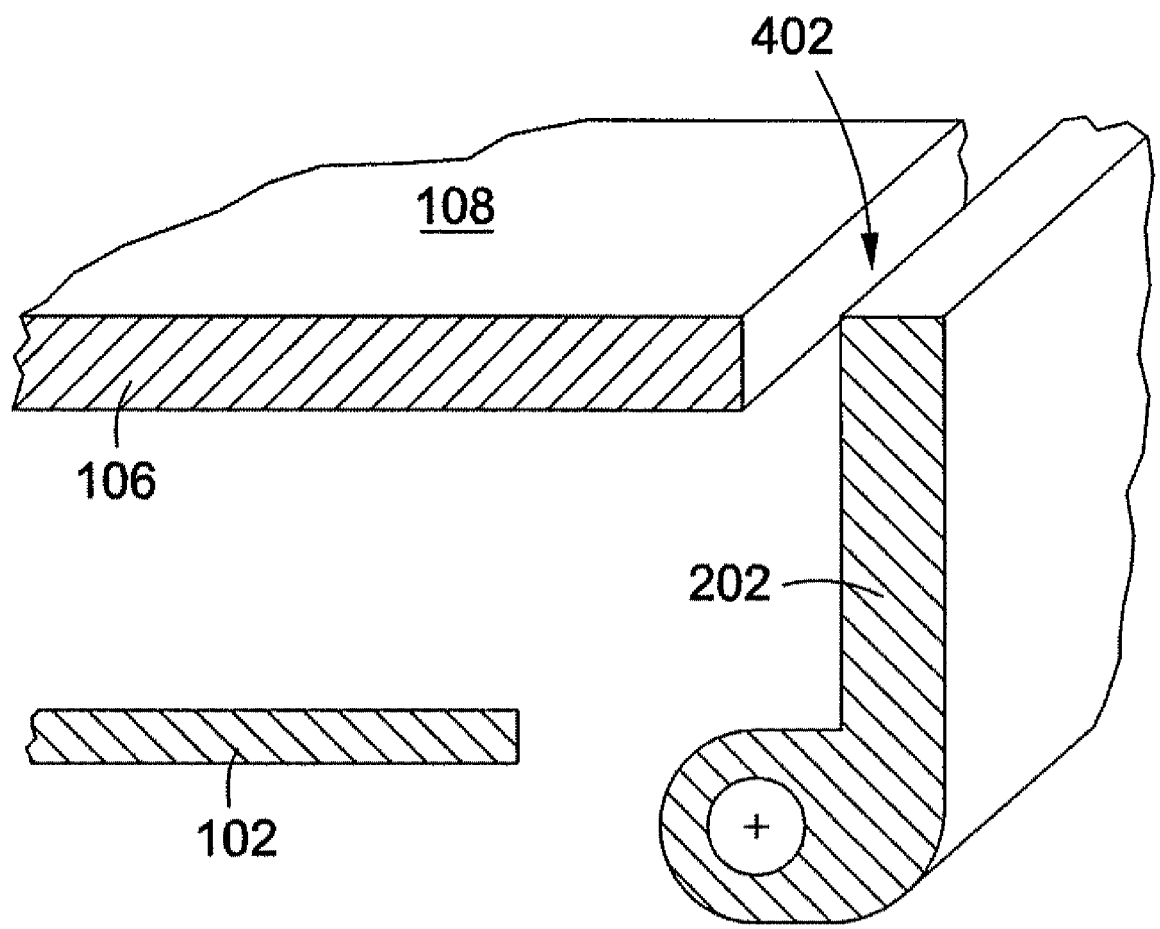
FIG. 4 illustrates a side view in the direction of arrows IV-IV of FIG. 2 of portions of the access panel, platform, and container of the weight-based dispensing system of FIG. 2.

FIG. 4 illustrates a side view in the direction of arrows IV-IV of FIG. 2 of portions of the access panel 202, platform 106, and container 108 of the weight-based dispensing system 100 of FIG. 2. The access panel 202 is prevented from contacting the platform 106 by creating an access panel clearance space 402 between the access panel 202 and the platform 106, thereby facilitating the accuracy of measurement by the weight sensors 102, e.g., by reducing or eliminating stick/slip interactions.

Accordingly, the disclosed embodiments provide a weight-based dispensing system configured to track items added to or removed from a station based on weight and the accessibility of containers in the station. Although primarily described with the example of medications and other medical supplies, embodiments of the present disclosure can be employed with other stored items.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A weight-based dispensing system comprising:
    a platform;
    a container, coupled to the platform, comprising a lid configured to move between a closed state restricting access to items in the container and an open state allowing access to the items in the container;
    at least two weight sensors, wherein each of the weight sensors is coupled to the platform and is configured to determine a change in weight on the platform; and
    a controller configured to determine a change in the number of items in the container based on the state of the lid and the change in weight on the platform,
    wherein a communications connector is configured to couple the container to the controller.

2. The system of claim 1, further comprising a plurality of containers coupled to the platform, each container comprising a lid configured to move between a closed state restricting access to items in the container and an open state allowing access to the items in the container, wherein the controller is configured to determine a change in the number of items in at least one of the plurality of containers based on the state of the lid of the at least one of the plurality of containers and the change in weight on the platform.

3. The system of claim 1, further comprising a plurality of platforms, wherein each platform comprises a plurality of containers coupled to the platform, each container comprising a lid configured to move between a closed state restricting access to items in the container and an open state allowing access to the items in the container, wherein the controller is configured to determine a change in the number of items in at least one of the plurality of containers on one of the plurality of platforms based on the state of the lid of the at least one of the plurality of containers and the change in weight on the platform.

4. The system of claim 1, wherein the determining of the change in the number of items comprises determining how many items have been added to or removed from the container.

5. The system of claim 1, wherein each of the two weight sensors is respectively coupled substantially near each end of the platform.

6. The system of claim 1, wherein the controller is configured to control movement of the lid between the closed state and the open state.

7. The system of claim 6, wherein the control of the movement of the lid between the closed state and the open state is wireless.

8. The system of claim 1, wherein the communications connector comprises a wired connection.

9. The system of claim 1, further comprising an access panel configured to restrict access to the at least two weight sensors.

10. The system of claim 9, wherein the access panel is configured to move between a closed state restricting access to the at least two weight sensors and an open state allowing access to the at least two weight sensors.

11. The system of claim 1, further comprising a third weight sensor coupled to the platform and configured to determine a change in weight on the platform.

12. The system of claim 1, wherein the controller is configured to store a value indicating the weight of each item of the items.

13. The system of claim 1, wherein the container is configured to be decoupled and removed from the platform.

14. The system of claim 1, wherein the lid is configured to identify the items in the container.

15. A weight-based dispensing system comprising:
    a cabinet comprising:
        a plurality of shelves, each shelf comprising:
            a common platform;

at least one container, coupled to the common platform, comprising a lid configured to move between a closed state restricting access to items in the at least one container and an open state allowing access to the items in the at least one container; and at least two weight sensors, wherein each of the weight sensors is coupled to the common platform and is configured to determine a change in weight on the common platform;

a controller configured to determine a change in the number of items in the at least one container based on the state of the lid and the change in weight on the platform; and a communications connector is configured to couple the container to the controller.

16. The system of claim 15, wherein the lid is configured to be electronically moved between the closed state and the open state.

17. A method for dispensing items comprising:

providing access to a plurality of items in a container coupled to a platform;

determining whether the weight of the container has changed using at least two weight sensors coupled to the platform; and determining, with a controller and based on the weight of the container, whether there is a change in the number of items in the container, wherein a communications connector is configured to couple the container to the controller.

18. The method of claim 17, further comprising determining the weight of each item of the plurality of items.

19. The method of claim 17, wherein the determining whether there is a change in the number of items in the container comprises determining how many items have been added to or removed from the container.

20. The method of claim 17, wherein each of the two weight sensors is coupled substantially near each end of the platform.

21. The method of claim 17, wherein the providing access to the plurality of items in the container comprises moving a lid of the container between a closed state restricting access to the plurality of items in the container and an open state allowing access to the plurality of items in the container.

22. The method of claim 17, wherein the determining whether the weight of the container has changed comprises using at least three weight sensors coupled to the platform.

* * * * *